United States Patent
Siskowski et al.

(12)

(10) Patent No.: US 6,616,609 B2
(45) Date of Patent: Sep. 9, 2003

(54) METHOD FOR OPTIMIZING PISTON DIAMETER IN A NON-CONTACT TONOMETER, AND NON-CONTACT TONOMETER HAVING FLUID PUMP DESIGNED BY SAID METHOD

(75) Inventors: Bruce Siskowski, Orchard Park, NY (US); David A. Luce, Clarence Center, NY (US)

(73) Assignee: Reichert, Inc., Depew, NY (US)

( * ) Notice: Subject to any disclaimer, the term of this patent is extended or adjusted under 35 U.S.C. 154(b) by 0 days.

(21) Appl. No.: 10/010,323

(22) Filed: Nov. 8, 2001

(65) Prior Publication Data
US 2003/0088171 A1 May 8, 2003

(51) Int. Cl.[7] ................................................. A61B 5/05
(52) U.S. Cl. ....................................................... 600/401
(58) Field of Search ................................ 600/399, 400, 600/401, 402, 403, 404, 405, 406, 398, 558; 417/553

(56) References Cited

U.S. PATENT DOCUMENTS

| | | | | | |
|---|---|---|---|---|---|
| 4,770,181 | A | * | 9/1988 | Tomoda | 600/401 |
| 5,002,056 | A | * | 3/1991 | Takahashi et al. | 600/401 |
| 5,048,526 | A | * | 9/1991 | Tomoda | 600/401 |
| 5,779,633 | A | * | 7/1998 | Luce | 600/398 |
| 6,361,495 | B1 | * | 3/2002 | Grolman | 600/401 |

* cited by examiner

Primary Examiner—Max F. Hindenburg
Assistant Examiner—Brian Szmal
(74) Attorney, Agent, or Firm—Hodgson Russ LLP

(57) ABSTRACT

A fluid pump system of a non-contact tonometer is numerically simulated through its compression stroke by a simulation software program. System dynamic behavior is modeled for a variety of piston diameters, whereby an optimal piston diameter or range of piston diameters is selected in view of stoke length limitations and target applanation pressure requirements.

4 Claims, 8 Drawing Sheets

METHOD FOR OPTIMIZING PISTON DIAMETER IN A NON-CONTACT TONOMETER, AND NON-CONTACT TONOMETER HAVING FLUID PUMP DESIGNED BY SAID METHOD

REFERENCE TO COMPUTER PROGRAM LISTING APPENDIX

The present application includes a computer program listing appendix on compact disc. Two duplicate compact discs are provided herewith. Each compact disc contains an ASCII text file of the computer program listing as follows:

Filename: NSL-Pneumatic Text File for Patent.txt

Size: 223,863 bytes

Date Created: Nov. 6, 2001

The computer program listing appendix is hereby expressly incorporated by reference in the present application

BACKGROUND OF THE INVENTION

I. Field of the Invention

The present invention relates generally to ophthalmic tonometers for measuring intraocular pressure (IOP) of a patient's eye, and more particularly to non-contact tonometers of the type having a piston movable in a compression stroke relative to a cylinder to compress air within a compression volume of the non-contact tonometer, and a discharge tube in flow communication with the compression volume for directing an air pulse at the patient's eye to deform the cornea.

II. Description of the Related Art

Non-contact tonometers are diagnostic instruments widely used by ophthalmologists and medical personnel for measuring the internal fluid pressure within the eye (intraocular pressure or IOP), often to screen patients for elevated IOP associated with glaucoma. Non-contact tonometers typically operate by directing a fluid pulse at the eye and observing deformation of the cornea. In conventional apparatus of the prior art, a fluid pump having a solenoid-driven piston compresses fluid within a compression volume, and a fluid discharge tube in communication with the compression volume and aligned with the patient's eye delivers a fluid pulse to the eye that deforms the cornea from its normal convex state, through a flattened state known as "applanation," to a concave state. When the fluid pulse dissipates, the cornea returns to its normal convex state. The deformation is monitored by opto-electronic means, and a quantity such as the plenum pressure at the moment of applanation or the time required to achieve applanation is measured and correlated to IOP.

Heretofore, non-contact tonometers have been primarily bulky "table top" instruments that are not easily portable. In practice, the patient sits at one end of the instrument with his or her head steadied by a forehead brace, and the operator sits at the opposite end to align the instrument relative to the eye and administer the test. The instrument, which contains precisely aligned optical components, remains stationary on the table except for a test portion that moves relative to a base of the instrument for alignment purposes. The primary design criterion for pump systems in non-contact tonometers of the prior art has been the capacity of the pump system to deliver the necessary force to the cornea to cause applanation, even where there exists high IOP; size and weight of the pump system have been secondary design considerations.

The desirability of a smaller, lightweight instrument for measuring IOP has been recognized for some time, as evidenced by the development of hand-held "contact" type tonometers. See for example, U.S. Pat. Nos. 4,192,317; 4,622,459; 4,747,296; and 5,174,292. Because a portion of the tonometer physically contacts the cornea, these instruments are generally regarded as being less comfortable to the patient than the noncontact variety described above, and there is an increased risk of infection because viruses and bacteria can be transferred from one patient to the next. Moreover, an operator's skill in testing can have a significant impact upon measurement results, thus rendering these instruments poorly suited for use by general medical practitioners.

U.S. Pat. No. 4,724,843 describes a portable non-contact tonometer that includes a carrying case 102 for housing a pump used to generate a fluid pulse, and a detachable hand-held unit 100 connected to the pump by a flexible connection line 104 enclosing a fluid conduit. Thus, only a portion of the instrument is hand-held, with the remainder of the instrument being large and heavy. The non-contact tonometer described in U.S. Pat. No. 4,724,843 is evidence that the size and weight of the pump mechanism presents a challenge for those attempting to design a truly hand-held non-contact tonometer that is compact and lightweight, yet is powerful enough, if necessary, to cause applanation of elevated IOP eyes.

The desire for a lighter tonometric pump mechanism runs counter to some of the advantages presented by a large diameter piston. These advantages include a shorter stroke length to achieve a target plenum pressure, and greater opposing force due to increased surface area for quickly stopping the piston after the driving solenoid has been switched off, thereby reducing unnecessary and uncomfortable "excess puff" delivered to the patient's eye. In fact, it can be shown that of the variables relating to pump mechanism design (i.e. piston diameter, piston mass, plenum volume, orifice size, etc.), the piston diameter has the greatest influence on stroke length, impulse delivered to the eye, and peak plenum pressure.

BRIEF SUMMARY OF THE INVENTION

Therefore, it is an object of the present invention to provide a non-contact tonometer with a piston having a piston diameter that is optimal for achieving a target plenum pressure within a given maximum stroke length without adding unwanted size and mass to the tonometer.

It is another object of the present invention to provide a systematic method for selecting a piston diameter in keeping with the aforementioned object.

In furtherance of these and other objects, a simulation software program is disclosed to numerically simulate the dynamics associated with a tonometer pump compression stroke for a plurality of piston diameters, whereby an optimal piston diameter or range of piston diameters is selected in view of stoke length limitations and target applanation pressure requirements. Consequently, the present invention encompasses both an improvement to a non-contact tonometer, and a method for selecting the piston diameter for a tonometer pump system using a numerical simulation technique.

BRIEF DESCRIPTION OF THE SEVERAL VIEWS OF THE DRAWINGS

The nature and mode of operation of the present invention will now be more fully described in the following detailed description of the invention taken with the accompanying drawing figures, in which.

DESCRIPTION OF THE INVENTION

Figure 1:
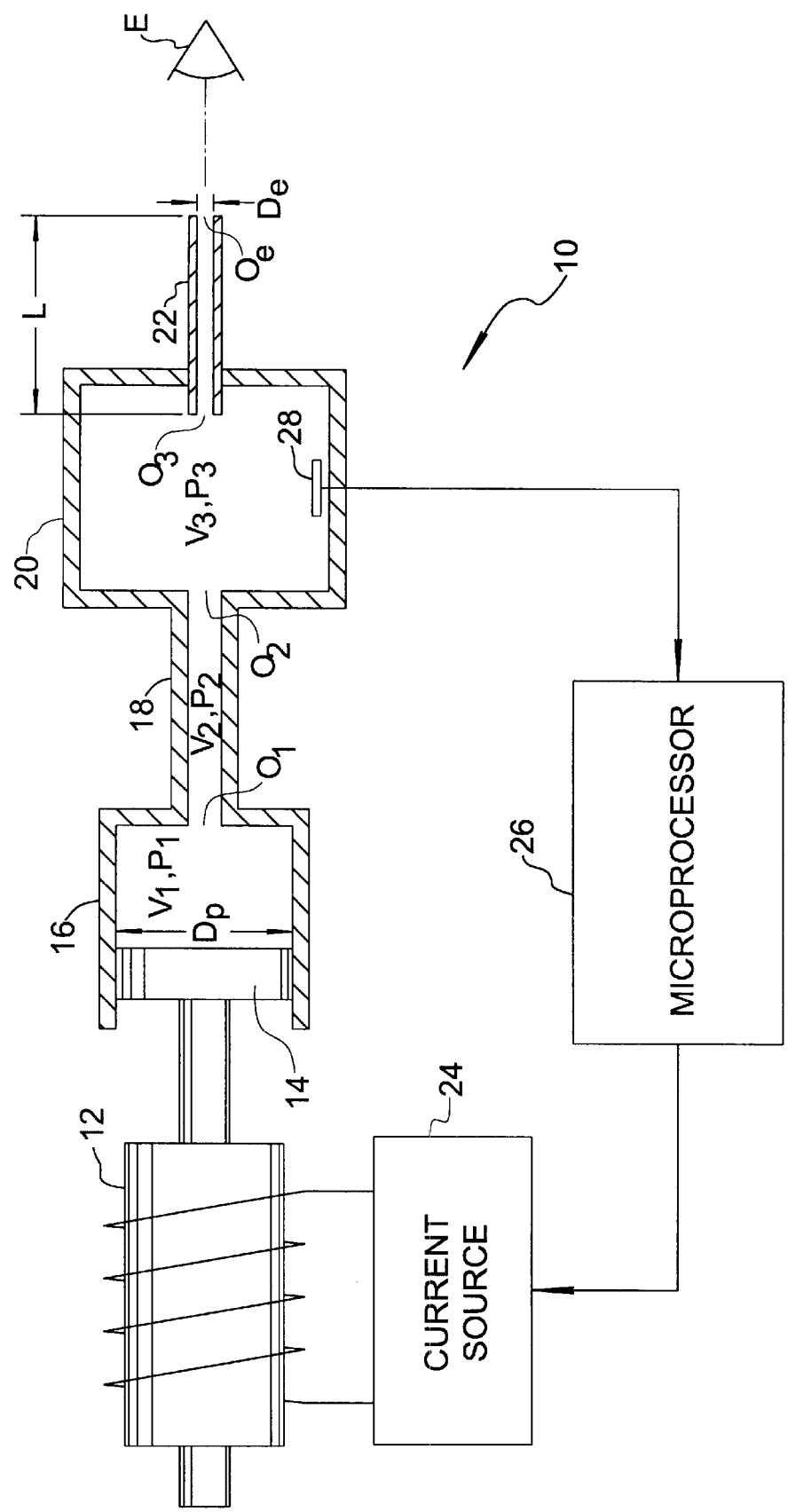
FIG. 1 is a schematic diagram of a fluid pump system of a non-contact tonometer.

FIG. 1 shows a tonometer pump system 10 comprising a linear solenoid 12, a piston 14 axially driven by linear solenoid 12 along a compression stroke, a cylinder 16 slidably receiving piston 14, a flow pipe 18 connected at one end to cylinder 16, a plenum housing 20 connected at an opposite end of flow tube 18, and a discharge tube 22 extending from plenum housing 20. Accordingly, the system defines a compression chamber volume $V_1$ at pressure $P_1$, a pipe volume $V_2$ at pressure $P_2$ in flow communication with compression volume $V_1$ through a first orifice $O_1$, and a plenum chamber volume $V_3$ at pressure $P_3$ in flow communication with pipe volume $V_2$ through a second orifice $O_2$ and in further flow communication with discharge tube 22 through a third orifice $O_3$. Piston 14 has a diameter $D_P$, while discharge tube 22 includes a circular exit orifice $O_e$ of diameter $D_e$. During a tonometric measurement, a current source circuit 24 energizes the coils of solenoid 12 under the control of a microprocessor 26 to force the piston to the right in FIG. 1, resulting in a fluid pulse being discharged through the exit orifice $O_e$ to deform the cornea of eye E. A pressure sensor 28 linked to microprocessor 26 monitors plenum pressure $P_3$ during the compression stroke, and a photosensitive element (not shown) provides a signal indicative of the occurrence of corneal applanation, whereby the plenum pressure at applanation is correlated to patient IOP. While the pump system described above is a currently preferred configuration for practicing the present invention, it will be understood that other configurations are equally appropriate for application of the method of the present invention.

In accordance with the present invention, the system above is modeled mathematically to provide a numerical simulation software program of a compression stroke, whereby various piston diameters can be evaluated. Two important initial parameters are the maximum stroke length of the piston, and the target IOP for which it is desired to cause applanation. The maximum stroke length can be thought of as the distance piston 14 is allowed to travel from an initial reference position (X=0) until it reaches the end of the cylinder 16. Since the point at which the piston reaches the end of the cylinder is accompanied by a loud noise, the word "bang" and the subscript "b" are used hereinafter to denote this condition. The target IOP is that pressure for which the system is designed to cause applanation. Intuitively, as the target IOP increases, the impulse delivered by the air pulse must also increase or the air pulse will not be strong enough to applanate the cornea.

Figure 2:
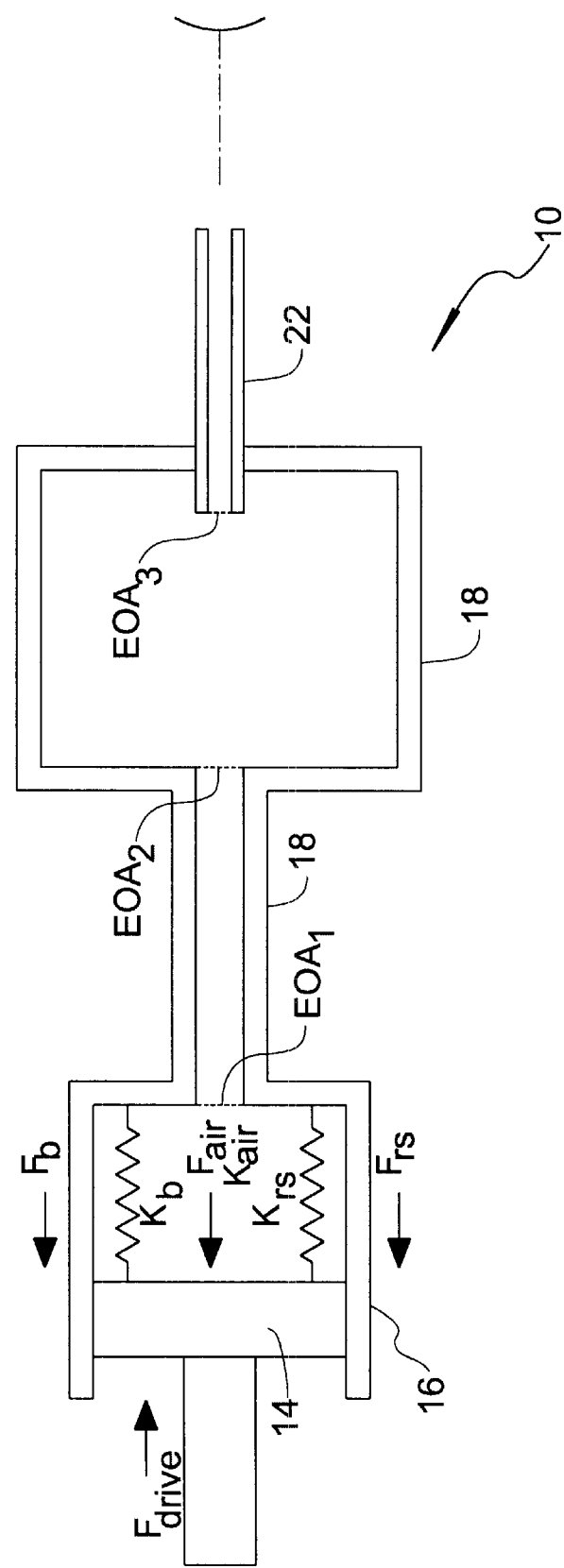
FIG. 2 is a schematic force diagram of the fluid pump system shown in FIG. 1.

FIG. 2 is a schematic force diagram of the fluid pump system shown in FIG. 1. A drive force is applied to piston 14 by solenoid 12. In a preferred fluid pump system, solenoid 12 is a proportional solenoid, wherein the drive force $F_{drive}$ applied to piston 14 is proportional to the current energizing the solenoid. The energizing current supplied to solenoid 12 by current source 24 preferably increases linearly with time, such that the drive force exerted by the solenoid increases linearly with time as well. Opposing forces include a return spring force $F_{rs}$ associated with a return spring built into the solenoid mechanism, a spring force $F_b$ encountered as the piston is about to complete its stroke, and a force $F_{air}$ exerted by air pressure in the cylinder acting against the surface area of the piston. In modeling the pneumatic system, it is useful to assign an effective orifice area (EOA) to each orifice $O_1-O_3$ for flow analysis through each orifice.

Figure 3:
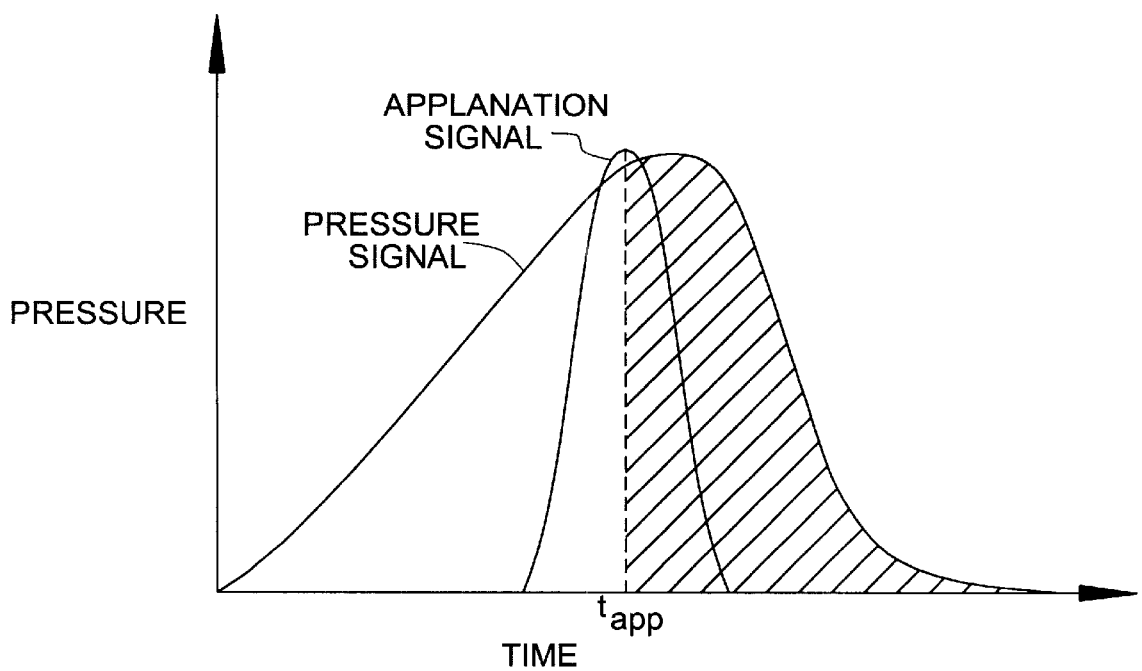
FIG. 3 is a graph showing a plenum pressure versus time and an applanation signal versus time for a tonometer piston compression stroke.

Referring now to FIG. 3, a typical pressure signal and applanation signal are plotted over time for a piston compression stroke associated with a tonometric measurement. It will be understood that the area under the pressure-time curve is indicative of the impulse energy delivered to the patient's eye during measurement. The hatched portion in the graph of FIG. 3 represents impulse energy delivered to the eye after applanation has already been achieved, and therefore it is unnecessary for measurement purposes. The impulse energy delivered to the patient is felt as pain or discomfort. Consequently, it is preferred that the simulation program calculate the total area under the pressure time curve, as this information is useful in evaluating different piston diameters from the standpoint of patient comfort.

Figure 4A:
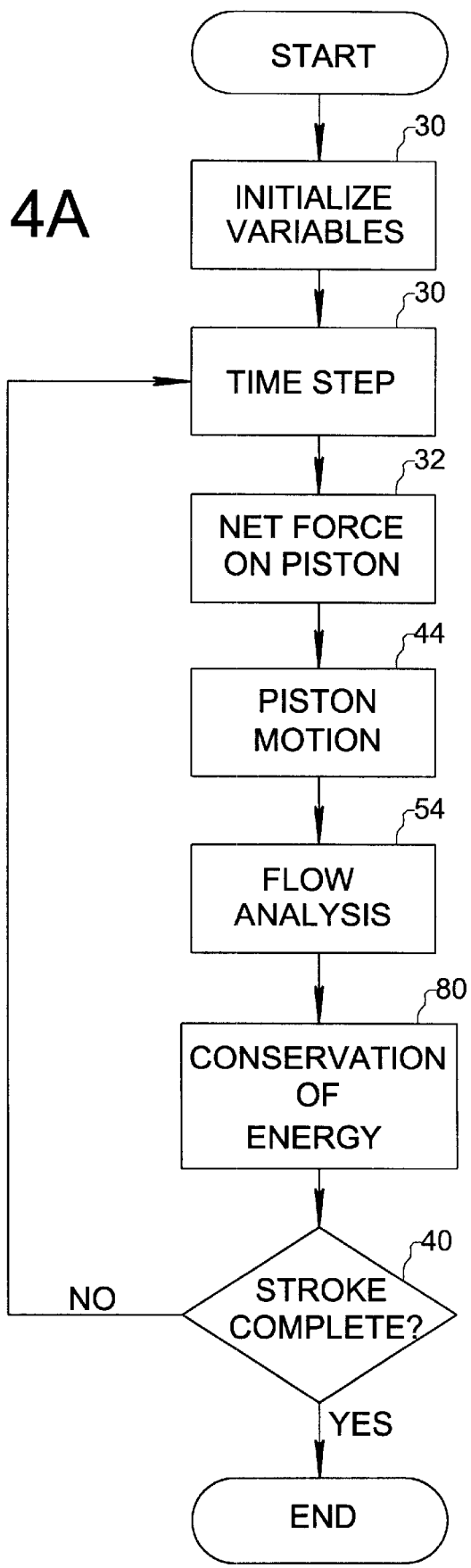
FIG. 4A is a general block diagram of a numerical simulation software program in accordance with an embodiment of the present invention.
Figure 4B:
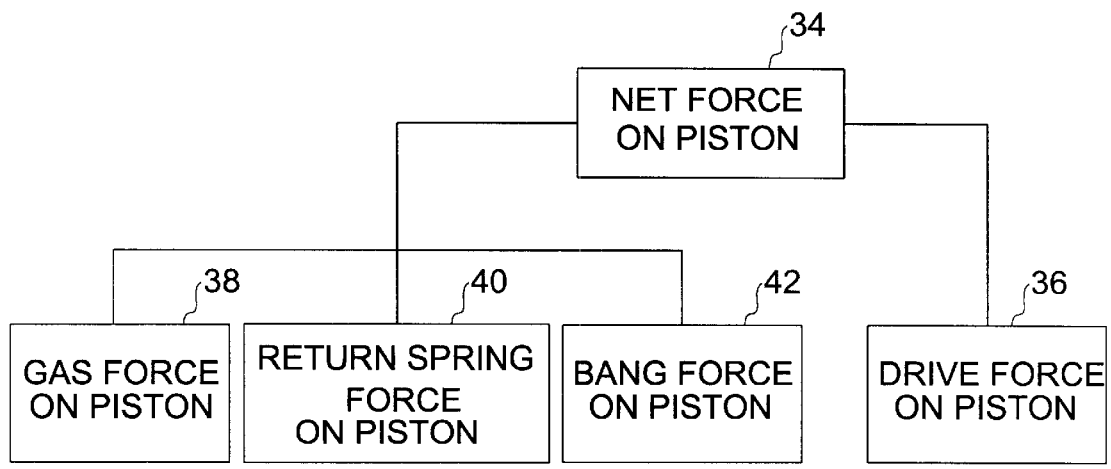
FIG. 4B is a block diagram of a force calculation portion of the simulation software program of FIG. 4A.

FIGS. 4A–4E depict the organization of a numerical simulation program for the fluid pump system of FIG. 1. General program flow is charted in FIG. 4A. After initialization of variables and assignment of starting conditions in block 30, a predetermined time step is registered in accordance with block 32. The simulation program then follows a series of blocks for calculating the physical state of the system at the particular iterative time. First, the net force on piston 14 is established according to block 34. FIG. 4B provides greater detail as to the net force calculation, wherein the net force is calculated by summing the force vectors associated with the solenoid drive force (block 36), air pressure on the piston (block 38), the return spring of the solenoid (block 40), and the "bang" force (block 42).

Figure 4C:
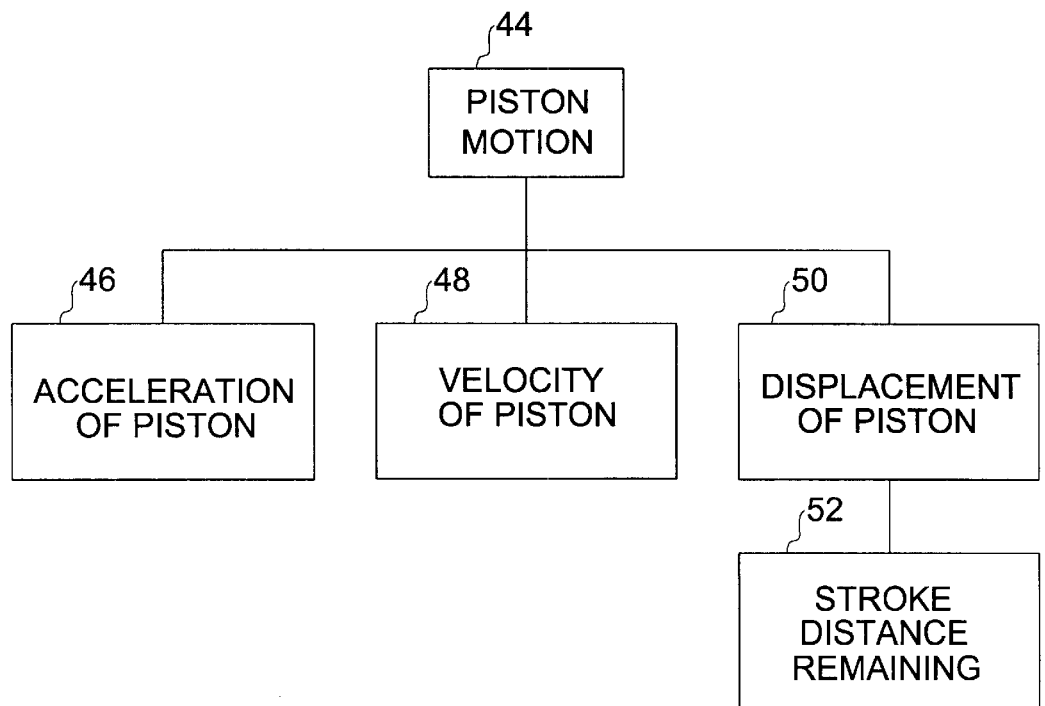
FIG. 4C is a block diagram of a piston motion portion of the simulation software program of FIG. 4A.

Once the net force acting on piston 14 is known, equations of motion are used to describe the present state of piston motion in accordance with block 44. FIG. 4C depicts program sub-blocks relating to piston motion, including piston acceleration (block 46), piston velocity (block 48), piston displacement (block 50), and the stroke distance remaining before the maximum stroke length is reached (block 52).

Figure 4D:
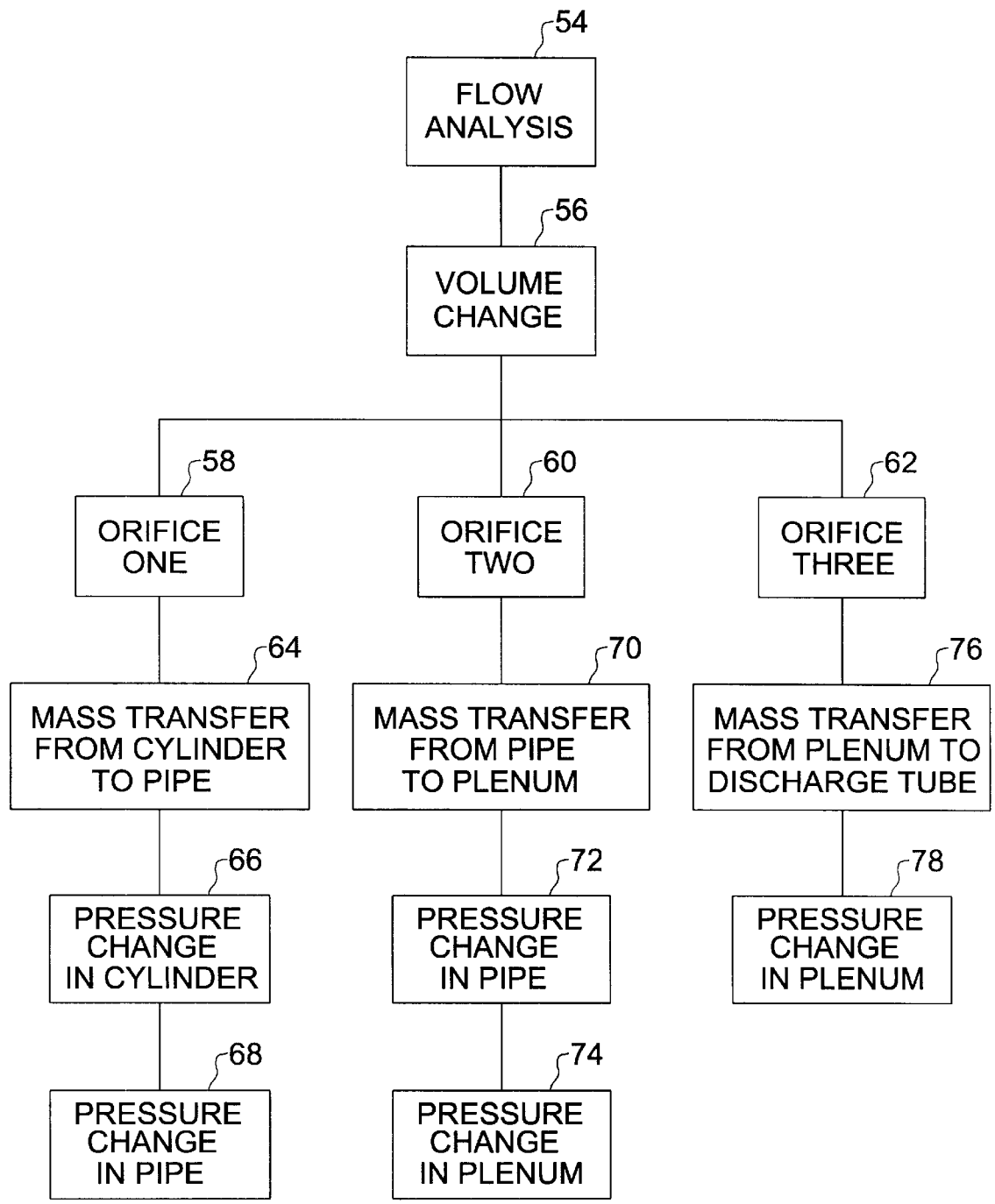
FIG. 4D is a block diagram of a flow analysis portion of the simulation software program of FIG. 4A.

The piston motion parameters are then used to conduct an isentropic flow analysis of the system under block 54. Flow analysis block 54 is programmed to determine mass transfer through orifices $O_1-O_3$ and pressure changes in volumes $V_1-V_3$ as a result of airflow through the system caused by piston motion. FIG. 4D provides further organizational detail of the flow analysis portion of the simulation program. The volume change at $V_1$ due to piston movement is determined in block 56, and then the program examines orifices $O_1$, $O_2$, and $O_3$ individually as indicated by blocks 58, 60, and 62, respectively. Under the analysis for orifice $O_1$, the mass transfer from cylinder 16 to pipe 18 (block 64), the pressure change in cylinder 16 (block 66), and the pressure change in pipe 18 (block 68) are determined. Under the analysis for orifice $O_2$, the mass transfer from pipe 18 to plenum housing 20 (block 70), the pressure change in pipe 18 (block 72), and the pressure change in plenum housing 20 (block 74) are determined. Finally, under the analysis for orifice $O_3$, the mass transfer from plenum housing 20 to tube 22 (block 76) and the pressure change in plenum housing 20 (block 78) are determined.

The simulation further comprises a conservation of energy analysis of the fluid pump system pursuant to block

Figure 4E:
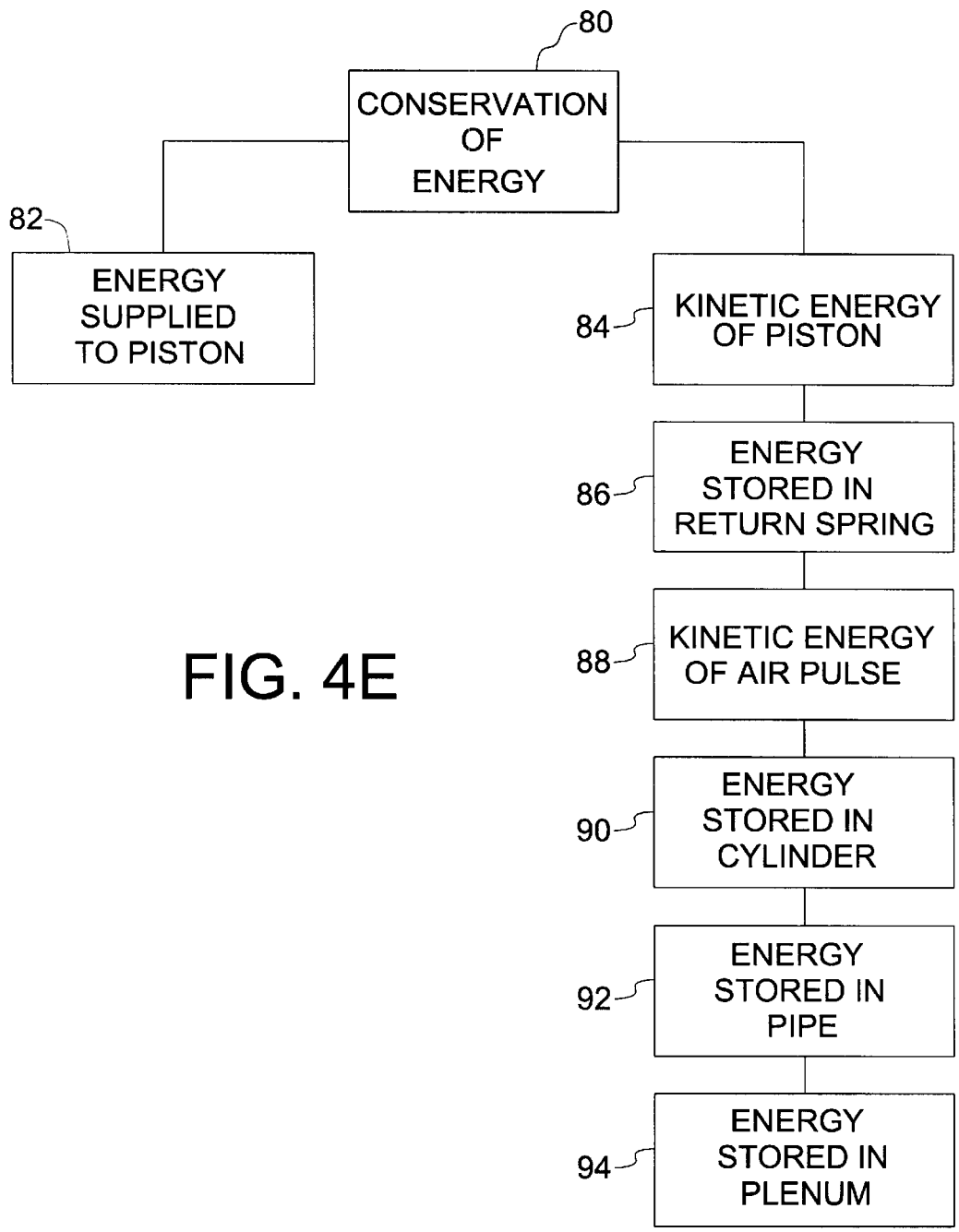
FIG. 4E is a block diagram of a conservation of energy portion of the simulation software program of FIG. 4A.

80. FIG. 4E provides greater detail in this regard. The energy supplied to piston 14 is accounted for in block 82 as work applied to the system, i.e. by summing the product of the drive force and the incremental displacement of the piston over time. Energy is present in the form of kinetic energy associated with piston movement (block 84), energy stored in the return spring of solenoid 12 (block 86), kinetic energy associated with the air pulse (block 88), and energy stored in cylinder compressed air in cylinder 16 (block 90), pipe 18 (block 92), and plenum housing 20 (block 94).

Figure 5:
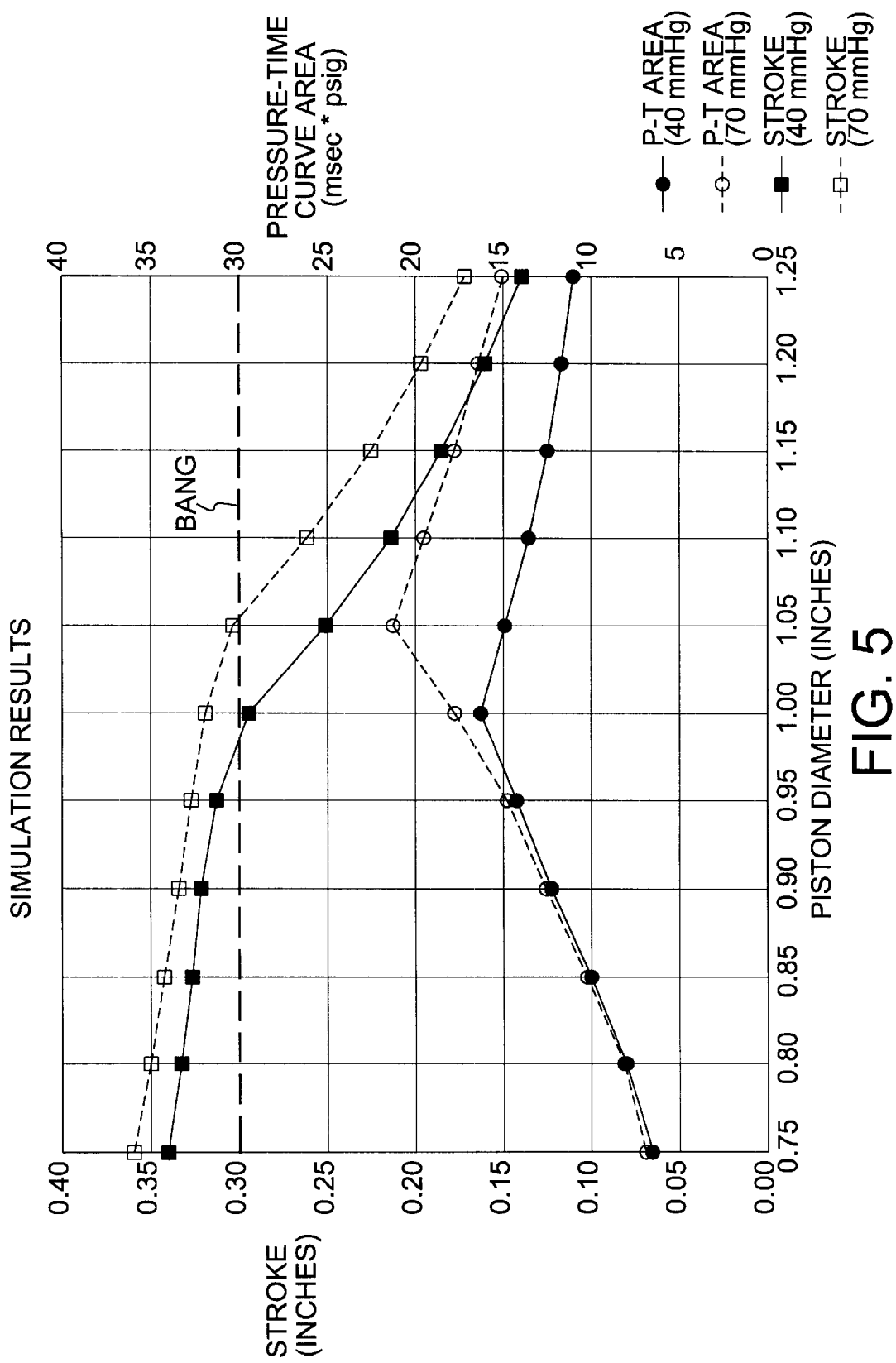
FIG. 5 is a graph showing stroke length and area below the pressure-time curve as a function of piston diameter for two different target plenum pressures.

FIG. 5 illustrates simulation results for a fluid pump system modeled in accordance with the present invention using the VISUAL BASIC® simulation program appended to the present specification. The simulation was performed for piston diameters ranging from 0.75 inches to 1.25 inches in increments of 0.05 inches, and for target pressures of 40 mmHg and 70 mmHg. In the modeled system, the initial pressures $P_1$–$P_3$ in volumes $V_1$–$V_3$ is at atmosphere, the temperature in each volume is 70° F., the area of orifice $O_1$ is 0.0438 square inches, the area of orifice $O_2$ is 0.0438 square inches, the area of orifice $O_3$ is 0.0071 square inches, the maximum stroke length is 0.3211 inches, and the piston weight for a 1.10 inch diameter piston is 0.098 lbs.

The necessary stroke length to achieve applanation, and the area under the pressure-time curve, are plotted in FIG. 5 for each set of simulations. As expected, for a each given diameter piston, the stroke length required to achieve applanation and the area under the pressure-time curve are greater for the 70 mmHg target pressure than for the 40 mmHg target pressure. Using a maximum stroke length of about 0.3 inches, as dictated by the travel range of the solenoid plunger, it is apparent that for piston diameters of 0.95 inches or less, the stroke length necessary to achieve applanation of a 40 mmHg eye is greater than the maximum stroke length allowed by the system. Likewise, it is apparent that for piston diameters of 1.05 inches or less, the stroke length needed to applanate a 70 mmHg eye exceeds the maximum stroke length of the system. The points can be seen located above the horizontal "bang" line in FIG. 5. As piston diameter increases, the necessary stroke length decreases. The stroke length for both 40 mmHg and 70 mmHg target pressures is below the maximum stroke length as the piston diameter surpasses 1.05 inches. In addition, the area curves for both the 40 mmHg and 70 mmHg simulations have peaked and are in decline for diameters greater than 1.05 inches. In keeping with the objects of the present invention, a 1.10 inch-diameter piston is sufficient to cause applanation of both 40 mmHg and 70 mmnHg eyes within the allotted maximum stroke length, and the decrease in the area under the pressure-time curve seen for larger diameter pistons is relatively flat. The 1.10-inch diameter is chosen as the center of an optimal diameter range of that starts at 1.06 inches (where the stroke lengths are both below the maximum allowable stroke length) and ends at 1.14 inches. Establishing a range of diameters is useful where an "off the shelf" piston is used rather than a custom-machined piston.

The resulting piston diameter and piston diameter range developed through simulation can be expressed in relative terms, as opposed to absolute terms, by a dimensionless system ratio SR that also takes into account the net volume $V_{net}$ of the system, the length L of discharge tube 22, and the diameter $D_e$ of the circular exit orifice $O_e$ of the discharge tube. The ratio is written as follows:

$$SR=(D_p{}^* D_e{}^* L)/V_{net}$$

where $V_{net}=V_1+V_2+V_3$ for the pneumatic system described herein. $V_{net}$ is also referred to herein as the "compression volume" of the system.

In the system simulated herein, $D_e$=0.095 inches, L=1.075 inches, $V_1$=8.4066 cc (0 . . 5130 cubic inches), $V_2$=1.4978 cc (0.0914 cubic inches), and $V_3$=1.8648 cc (0.1138 cubic inches). Therefore, a system ratio SR in the range of 0.1507 through 0.1621, and preferably about 0.1564, is considered optimal in accordance with the present invention for a fluid pump system of a non-contact tonometer, in particular a hand-held non-contact tonometer. The system ratio and system ratio range established in accordance with the present invention represents a notable departure from prior art systems with which applicants are familiar. For example, the XPERT® non-contact tonometer manufactured by Reinsert Ophthalmic Instruments, a division of Leica Microsystems Inc. (assignee of the present application), has a system ratio SR=0.0696. By way of further example, the AT-550 non-contact tonometer, also manufactured by Reinsert Ophthalmic Instruments, has a system ratio SR=0.0707. Both the XPERT® and AT-550 non-contact tonometers are table-top, as opposed to hand-held, instruments.

What is claimed is:

1. In a non-contact tonometer of the type having a piston of diameter $D_p$ movable in a compression stroke relative to a cylinder to compress air within an air compression volume of said non-contact tonometer, and a discharge tube in flow communication with said air compression volume for directing an air pulse at an eye to be tested, said discharge tube having a length L and an exit orifice of diameter $D_e$, the improvement comprising:

said piston diameter $D_p$ being chosen such that a system ratio SR given by $$SR=(D_p{}^*D_e{}^*L)/V_{net}$$

is in the range of 0.1507 through 0.1621.

2. The improvement according to claim 1, wherein said system ratio SR is about 0.1564.

3. A method of selecting the diameter of a piston used in a non-contact tonometer, said piston being movable in a compression stroke to compress air within a compression volume to discharge an air pulse from a discharge tube in flow communication with said compression volume, said method comprising the steps of:

A) establishing a maximum stroke length of said piston;

B) setting a target plenum pressure;

C) calculating a required stroke length of said piston that is the minimum stroke length necessary to achieve said target plenum pressure, said required stroke length being calculated for a plurality of piston diameters; and D) selecting the smallest piston diameter that corresponds to a stroke length less than said maximum stroke length.

4. The method according to claim 3, wherein said step (C) is performed by running a numerical simulation of said piston compression stroke for said plurality of piston diameters.

* * * * *

UNITED STATES PATENT AND TRADEMARK OFFICE
CERTIFICATE OF CORRECTION

PATENT NO.    : 6,616,609 B2
DATED         : September 9, 2003
INVENTOR(S)   : Siskowski et al.

It is certified that error appears in the above-identified patent and that said Letters Patent is hereby corrected as shown below:

<u>Title page,</u>
Item [*] Notice, should read as follows:
-- Subject to any disclaimer, the term of this patent is extended or adjusted under 35 U.S.C. 154(b) by 98 days. --.

Signed and Sealed this

Sixteenth Day of December, 2003

JAMES E. ROGAN
*Director of the United States Patent and Trademark Office*